United States Patent [19]

Damiani et al.

[11] 4,092,378

[45] May 30, 1978

[54] METHOD OF REFINING PHOSPHATE-ESTER FLUIDS

[76] Inventors: Robert A. Damiani, 6 N 022 Briarwood Dr., St. Charles, Ill. 60174; P. Dwaine Fowlkes, 702 Elm, Glen Ellyn, Ill. 60137

[21] Appl. No.: 665,538

[22] Filed: Mar. 10, 1976

[51] Int. Cl.² ............................ C07F 9/11; C07F 9/12; C07F 9/17; C07F 9/18
[52] U.S. Cl. ............................................... 260/990
[58] Field of Search ......................................... 260/990

[56] References Cited

U.S. PATENT DOCUMENTS

| | | |
|---|---|---|
| 2,854,468 | 9/1958 | Max ....................................... 260/990 |
| 3,706,822 | 12/1972 | Caldwell ............................... 260/990 |
| 3,996,341 | 12/1976 | Lee ..................................... 260/990 X |

*Primary Examiner*—Richard L. Raymond
*Attorney, Agent, or Firm*—Olson, Trexler, Wolters, Bushnell & Fosse, Ltd.

[57] ABSTRACT

A process of refining phosphate-ester fluids includes the steps of contacting the fluid with a source of saturated, straight-chain hydrocarbon material and subsequently splitting the mixture by the introduction of water. Organic contaminants originally present in the phosphate-ester fluid ultimately reside in the straight-chain hydrocarbon phase.

10 Claims, No Drawings

METHOD OF REFINING PHOSPHATE-ESTER FLUIDS

BACKGROUND OF THE INVENTION

A substantial number of phosphate-ester materials have been developed heretofore for use as fire-resistant hydraulic fluids, lubricants and the like; and while these materials possess many desirable properties, they have proved to be comparatively expensive; and this factor has encouraged reclamation of spent fluid rather than its discharge to waste. Environmental considerations, especially the reduction of phenolics and hexane-extractables in effluent waters, also indicate reclamation as the procedure of preference.

In use, phosphate-ester type fluids eventually become contaminated with such things as tramp oil, dirt, metal particles and metal salts of decomposed phosphate esters; and these fluids also degrade oxidatively with an increase in the acid number. Heretofore, used fluids of this nature have been reclaimed by treatment, for example, with aqueous caustic and by filtration through a material like fullers earth. Such procedures reduce solid and certain acidic contaminants but are not efficient in removing organic contaminants, especially those which contain combined iron or other metal salts.

Tramp oil contaminants adversely affect the fire-resistant character of the phosphate esters by lowering the autoignition temperature, flashpoint, fire point, and generally decrease the resistance to ignition by fire or heat sources. Additionally, the presence of tramp oil lowers the specific gravity of phosphate esters, which are ordinarily heavier than water, and increases the difficulty of separating or recovering them from effluent waters.

A common class of organic contaminants of phosphate-ester fluids includes the partial esters; and these may be present because of originally incomplete esterification or because of oxidation degradation. These partial esters, in turn, affect hydrolytic stability and water demulsability which reduce recoverability from effluent water streams. The partial acid esters also exhibit the unwanted faculty of complexing with such metal ions as calcium, magnesium, copper, aluminum and iron. These complexes tend to form solids or gels which, in turn, adversely affect the physical properties of the fluid and can even result in severe filtration problems in operating hydraulic systems.

SUMMARY OF THE INVENTION

In order to overcome the deficiencies of prior reclamation procedures, we have established that contacting contaminated phosphate-ester fluid with a saturated, straight-chain hydrocarbon material, such as mineral seal oil, followed by water-splitting substantially removes such undesirable organic components as partial esters and tramp oils from the fluid.

Accordingly, a principal object of the present invention is to provide a new and improved process of refining phosphate-ester fluids.

Another object of the invention is to provide a process of refining phosphate-ester fluids which may be employed either in the original manufacturing operations or as a reclamation procedure.

These and other objects and features of the invention will become more apparent from a consideration of the following description.

DESCRIPTION OF THE PREFERRED EMBODIMENTS

The phosphorus esters which may be refined by the method of the present invention have the general formula

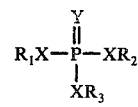

wherein $R_1$, $R_2$ and $R_3$ individually represent an alkyl group, an aryl group, an alkylaryl group, an arylalkyl group, an alkoxyalkyl group, an alkoxyaryl group, a haloaryl group, a haloalkyl group, a nitroalkyl group, a nitroaryl group, a cyanoaryl group, a haloalkylaryl group or an alkylthioalkyl group; wherein Y represents oxygen or sulfur; and wherein X represents oxygen, sulfur or a carbon-phosphorus bond, at least one of X being oxygen or sulfur. The phosphorus esters contemplated by the present invention frequently contain one and usually more than one aryl group and are known to be generally immiscible with paraffinic petroleum oils. Examples of such phosphorus esters are the commercial lines of hydraulic fluid sold by Monsanto Company under the trade designation "Pydraul", by Stauffer Chemical Co. under the trade designation "Fyrquel" and by E. F. Houghton & Co. under the trade designation "Houghto-Safe".

In accordance with the refining process of the invention, phosphate-ester fluids are preferably first contacted with alkaline material in order to neutralize partial esters and other acidic residues; and this may be accomplished by agitating the phosphate-ester fluid with aqueous caustic; and in compliance with the features of the present invention, the alkaline material treatment is regulated to adjust the pH to at least as high as about 8.0 and preferably about 9.5. After alkaline treatment, the fluid is passed through a bed of a suitable adsorbent such as fullers earth to remove solids and any substantial aqueous constituent that may be present.

According to an important feature of the invention, the phosphate-ester fluid is then contacted with a source of saturated, straight-chain hydrocarbon material for sufficient time to physically combine organic contaminants with the straight-chain hydrocarbon. This may be accomplished by introducing a measured volume of the phosphate-ester fluid into a reactor vessel and then adding the hydrocarbon material with mechanical agitation. The mixture is then allowed to stand in a quiescent state for a suitable period of time depending upon the relative viscosities of the fluid and the hydrocarbon material, the temperature, and the amount of contamination to be removed. At ambient room temperature, this holding time can be as much as 12-14 hours. For phosphate-ester fluids containing an ordinary quantity of contamination, approximately 30 volumes of the hydrocarbon material is added to 100 volumes of the fluid for use in bringing it up to new product specifications.

Suitable sources of saturated, straight-chain hydrocarbon material are non-additive natural or synthetic paraffinic petroleum oils; and examples include such products as mineral seal oil and light processing oil. These hydrocarbon materials exhibit greater affinity than the phosphate-ester fluid for complexed partial esters, tramp oils and other organic contaminants.

After completion of the holding period, water is added to the mixture with initial agitation only; and this results almost immediately in the separation of a water phase, a straight-chain hydrocarbon material phase containing organic contaminants, and a phase comprising a purified phosphate-ester fluid residing at the bottom of the reactor vessel overlaid immediately by the water phase and ultimately by the hydrocarbon material phase. Commonly, 30 volumes of water is added to 130 volumes of the mixture to accomplish separation. It has been found that some sodium salts take residence in the water phase whereas the metal complexes, such as those of iron, are principally confined to the hydrocarbon material phase. While de-ionized water is not required in the process of the present invention, it is preferable to employ water of low mineral content.

The refined phosphate-ester fluid is decanted and desirably finished by water washing and de-moisturizing in the conventional manner.

The effectiveness of the refining process of the present invention in reducing the sodium ion and iron ion content of a used phosphate-ester fluid to acceptable levels is demonstrated in Table I hereinbelow. Considering these data, it will be noted that treatment only with caustic soda dramatically increases the sodium content and leaves the iron content substantially unchanged, the noted small increase in iron content probably being the result of contamination from equipment used in manufacture of the caustic. Treatment with caustic soda followed by oil treatment and water-splitting halves the iron content and reduces the sodium ion concentration to acceptable limits.

TABLE I

| Reclamation Procedure | sodium (p.p.m.) | iron (p.p.m.) |
|---|---|---|
| used "Pydraul" hydraulic fluid (untreated) | 55 | 14 |
| caustic treatment only, followed by water wash | 1,387 | 15 |
| caustic treatment plus petroleum oil treatment and water-splitting | 256 | 8 |

In order that the present invention may be thoroughly understood, the following specific examples are given without, however, limiting the invention to the precise details and conditions described except as is set forth in the appended claims.

EXAMPLE I

A 100 ml. sample of used Pydraul 50E fire-resistant hydraulic fluid was contacted with solid sodium hydroxide, until a pH of 9.5 was achieved, and thereafter run through a quantity of fullers earth. This pre-treated sample was introduced into a 250 ml. graduated cylinder with 30 ml. of Gulf mineral seal oil at approximately 80° F. The mixture was agitated by shaking the graduate vigorously and then was allowed to stand for approximately five minutes. Thereafter, 30 ml. of tap water was added with shaking and the resultant mixture was added to a 250 ml. separatory funnel. Separation of three phases began almost immediately and was complete in approximately 14 hours, whereupon the refined fluid was drawn off from the bottom of the funnel.

The starting pH of the used hydraulic fluid was 6.5 and the initial acid number of 0.85. By comparison, the pH of the refined hydraulic fluid was 8.0 and the final acid number was 0.063. Approximately 97% of the initial hydraulic fluid was recovered in the refined state.

EXAMPLE II

The procedure of Example I was followed except that 200 ml. of the hydraulic fluid was contacted with 60 ml. of Prorex 37 light processing oil from Mobile Refining Co. in place of the mineral seal oil. After completing all the treatments, the finished hydraulic fluid had a pH of 8.1 and an acid number of 0.11.

The embodiments of this invention in which a particular property or privilege is claimed are defined as follows.

The invention is claimed as follows:

1. In a process of refining phosphate-ester fluids to remove tramp oil and partial acid ester contaminants of such fluids, said phosphate-ester fluids being of the formula:

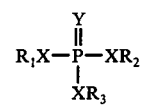

wherein $R_1$, $R_2$ and $R_3$ individually represent an alkyl group, an aryl group, an alkylaryl group, an arylalkyl group, an ankoxyalkyl group, an alkoxyaryl group, a haloaryl group, a haloalkyl group, a nitroalkyl group, a nitroaryl group, a cyanoaryl group, a haloalkylaryl group or an alkylthioalkyl group; wherein Y represents oxygen or sulfur; and wherein X represents oxygen, sulfur or a carbon-phosphorus bond, at least one of X being oxygen or sulfur, wherein the improvement comprises the steps of: contacting a quantity of a contaminated phosphate-ester fluid with a caustic material to adjust the pH of said fluid to at least about 8.0; contacting resultant alkaline fluid with a source of saturated, straight-chain hydrocarbon liquid material for sufficient time to combine said organic contaminants with said straight-chain hydrocarbon material; adding water to the resultant mixture, with agitation; allowing the water-mixture to stand without agitation to separate three distinct liquid phases consisting essentially of a water phase containing metal salts of partial ester, a straight-chain hydrocarbon material phase containing organometallic complexes of partial ester, and a phase comprising purified phosphate-ester fluid; and separating the purified phosphate-ester fluid phase from the other said phases.

2. The process according to claim 1 wherein said source of saturated, straight-chain hydrocarbon material is a petroleum oil.

3. The process according to claim 2 wherein said petroleum oil is mineral seal oil.

4. The process according to claim 2 wherein said petroleum oil is light processing oil.

5. The process according to claim 1 wherein 100 parts by volume of phosphate-ester fluid are mixed with 30 parts by volume of the source of saturated, straight-chain hydrocarbon material.

6. The process according to claim 5 wherein 30 parts by volume of water is added to the mixture.

7. The process according to claim 1 wherein said phases are separated by gravity and decanting.

8. The process according to claim 1 wherein, prior to treatment with said hydrocarbon material, wherein after said phosphate-ester fluid is contacted with a quantity of caustic material, any resultant aqueous phase is separated from said fluid.

9. The process according to claim 1 wherein the caustic material treatment is regulated to adjust the pH of the phosphate-ester fluid to about 9.5.

10. The process according to claim 1 which further comprises the steps of water-washing the purified phosphate-ester fluid phase.

* * * * *